United States Patent [19]

England

[11] Patent Number: 4,512,602
[45] Date of Patent: Apr. 23, 1985

[54] DEVICE FOR INSERTING AND REMOVING CONTACT LENSES

[76] Inventor: Robert C. England, P.O. Box 2829, Zanesville, Ohio 43701

[21] Appl. No.: 552,707

[22] Filed: Nov. 17, 1983

[51] Int. Cl.³ .............................................. A61F 9/00
[52] U.S. Cl. ................................................... 294/1.2
[58] Field of Search ...................... 294/1 CA, 2, 64 R; 206/5.1

[56] References Cited

U.S. PATENT DOCUMENTS

| | | | |
|---|---|---|---|
| 3,584,908 | 6/1971 | Ray | 294/1 CA |
| 3,645,576 | 2/1972 | Horres | 294/1 CA |
| 4,088,359 | 5/1978 | Buchanan | 294/1 CA |
| 4,097,081 | 6/1978 | England | 294/1 CA |
| 4,126,345 | 11/1978 | List | 294/1 CA |
| 4,190,277 | 2/1980 | England | 294/1 CA |
| 4,221,414 | 9/1980 | Schrier | 294/1 CA |

FOREIGN PATENT DOCUMENTS 3118185  1/1983  Fed. Rep. of Germany ... 294/1 CA

Primary Examiner—Johnny D. Cherry
Attorney, Agent, or Firm—Diller, Ramik & Wight

[57] ABSTRACT

The disclosure is directed to a device for inserting and removing contact lenses formed from an elongated body of resilient material having opposite terminal end portions and a central longitudinal axis, a first of the end portions having a relatively shallow concavely outwardly opening locating surface upon which a contact lens will be retained incident to inserting the lens upon an eye, a second of the terminal end portions being of a frusto-conical configuration on a narrow end of which is a suction cup having a concavely outwardly opening locating surface upon which a contact lens will be retained upon removing the lens from an eye, the concave surfaces having generally parallel radii of generation which are normal to a common plane defining a generally 45 degree angle with the central axis, and the latter relationship allows complete visibility during insertion or removal of contact lenses, particularly when a mirror is being utilized and more particularly when the user has very poor or limited vision.

5 Claims, 6 Drawing Figures

U.S. Patent  Apr. 23, 1985  4,512,602
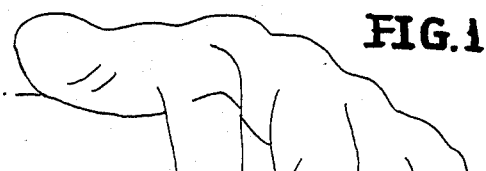
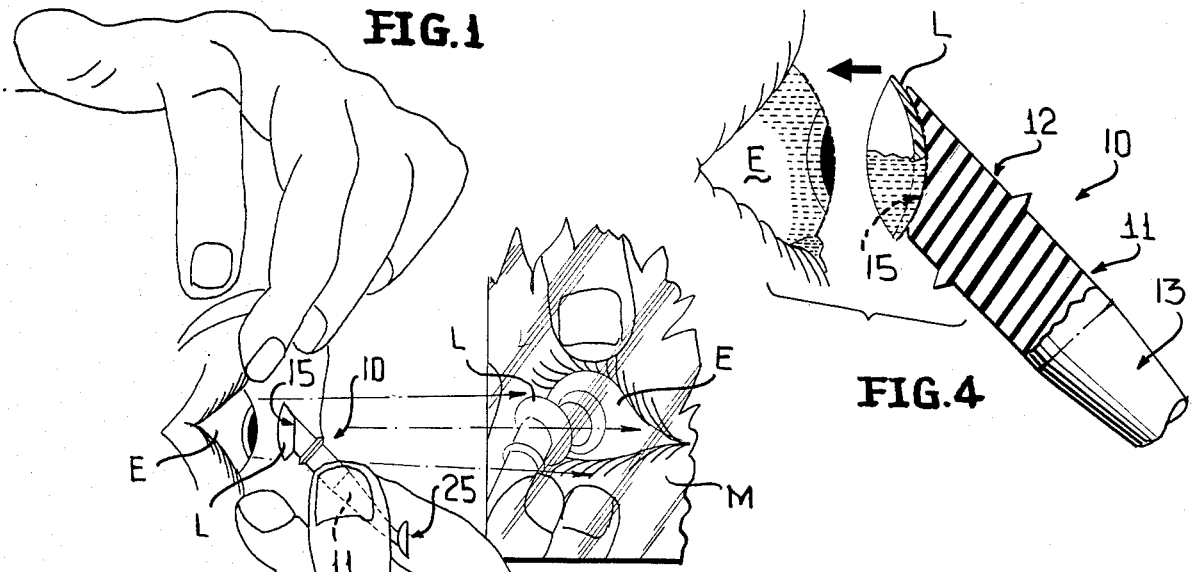
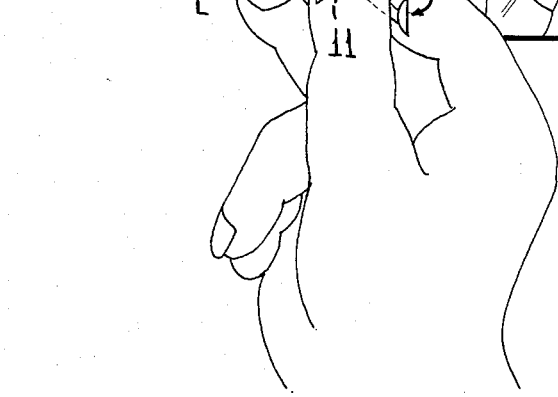
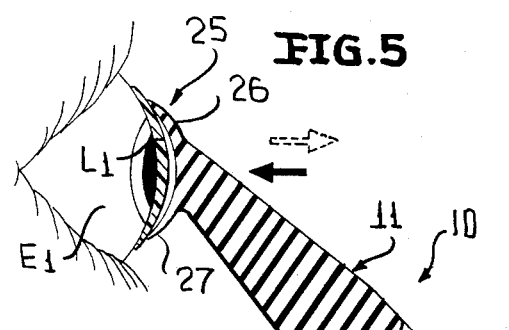
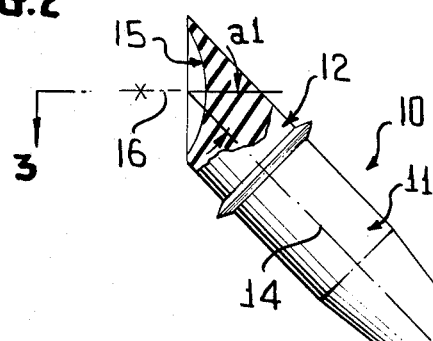
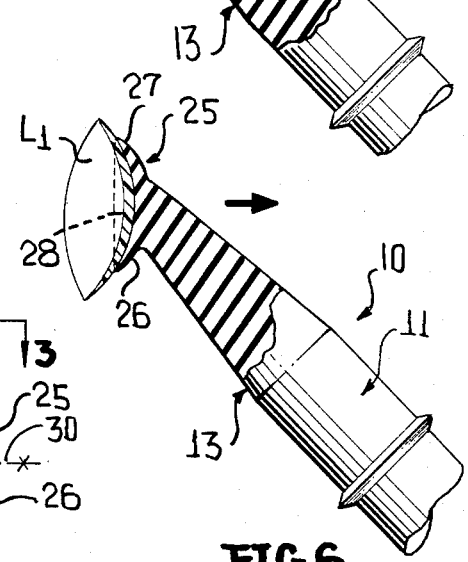
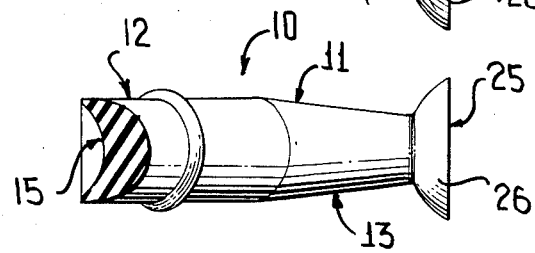

DEVICE FOR INSERTING AND REMOVING CONTACT LENSES

The present invention is directed to a novel device for inserting and removing contact lenses with devices of this type being disclosed in U.S. Pat. No. 4,190,277 and 4,097,081 issued respectively on Feb. 26, 1980 and June 27, 1978 to Robert C. England. The present invention is more specifically directed to an improvement of the suction cup device of Patent No. 4,097,081 in which the radius of generation of the suction cup is coincident to the axis of the body of the device which inherently obstructs visibility when one is utilizing the device in association with a mirror to insert or remove contact lenses relative to an eye.

Essentially, hard contact lenses have been removed from the human eye by two methods, namely, manual manipulation and by suction cup devices, such as that disclosed in U.S. Pat. No. 4,097,081. The suction cup devices utilize either static suction created by a resilient hollow curved suction cup or by active suction created by a resilient curve cup and a bulb or medicine dropper-like chamber. Insofar as the insertion of contact lenses is concerned, such has previously been done by placing the lens on the eye with one's fingertip, by use of hollow cup-like shaped devices attached to thimble-type finger attachments, or by hollow suctionless devices.

The primary disadvantage of known removal devices, be they of the static suction or active suction type, resides in the difficulty of accurately aligning the suction cups with a lens which is to be removed. This is particularly true when a mirror is being utilized, and the device of the type disclosed in U.S. Pat. No. 4,097,081 in which the device is virtually in line with the eye and the lens to be removed therefrom and, therefore, causes obstruction when the user looks into a mirror as is most often the case when a contact lens is being removed. Obviously, the same problem is associated with the utilization of a manual inserting device which must similarly be virtually aligned directly along the line of sight when a lens is to be inserted upon the eye.

In keeping with the foregoing, a primary object of the present invention is to provide a novel device for inserting and removing hard contact lenses from the human eye in such a manner that visibility relative to an associated mirror is essentially unobstructed and a lens can be readily and rapidly inserted or removed without fear of eye damage.

In keeping with the foregoing, the contact lens inserting and removing device is formed as an elongated body of resilient material having opposite terminal end portions and a central axis with first means at one of the terminal end portions for locating a contact lens at a predetermined angle to the central axis incident to inserting the lens upon an eye, second means at another of the terminal end portions for locating a contact lens at a predetermined angle to the central axis incident to removing the lens from an eye, and both of the predetermined angles being generally 45 degrees whereby during both insertion and removal of a lens relative to an eye, visibility is unobstructed relative to an associated mirror and, thus, eye damage is virtually minimized and/or precluded.

Still another object of this invention is to provide a novel device for inserting and removing contact lenses of the type aforesaid wherein both the first and second locating means are concave surfaces each defined by a radius of generation, the radii of generation are parallel to each other, and the radii of generation are also normal to a common plane defining the generally 45 degree angles with the central axis.

Still another object of this invention is to provide a novel contact lens inserting and removing device as aforesaid wherein the concave locating surfaces open in diametrically opposite direction and the surface upon which a lens rests for insertion upon an eye is of a shallower configuration than that to which a lens will adhere upon removal of a lens from an associated eye.

With the above and other objects in view that will hereinafter appear, the nature of the invention will be more clearly understood by reference to the following detailed description, the appended claims and the several views illustrated in the accompanying drawing.

IN THE DRAWING:

FIG. 1 is a perspective view of a device for inserting and removing contact lenses in accordance with this invention, and illustrates the manner in which a lens is held upon the device incident to inserting the lens upon an eye while maintaining unobstructed visibility relative to an associated mirror.

FIG. 2 is an enlarged view of the inserting and removing device of FIG. 1 with a portion thereof broken away and shown in cross section for clarity, and illustrates opposite terminal ends each including a generally outwardly opening concave locating surface upon and against which a contact lens rests during insertion and/or removal from an associated eye.

FIG. 3 is a sectional view taken generally along line 3—3 of FIG. 2 and more clearly illustrates details of the contact lens inserting and removing device.

FIG. 4 is a fragmentary sectional view of the device of this invention, and illustrates the manner in which a contact lens is located upon one of the concave surfaces incident to inserting the lens upon an associated eye.

FIG. 5 is a fragmentary sectional view of the device, and illustrates the manner in which a lens is removed by a suction cup at the opposite end of the device.

FIG. 6 is a fragmentary sectional view similar to FIG. 5, and illustrates the lens after it has been totally removed from the eye of FIG. 5.

A novel device constructed in accordance with this invention for inserting and removing hard contact lens is best illustrated in FIG. 2 of the drawing and is generally designated by the reference numeral 10.

The contact lens inserting and removing device 10 includes an elongated body 11 formed of resilient material, such as relatively soft rubber, having opposite terminal end portions 12, 13. The elongated body 11 also includes a central longitudinal axis, generally designated by the reference numeral 14.

First means 15 are provided at the terminal end portion 12 for locating a contact lens L (FIG. 4) at a predetermined angle to the central axis 14 incident to inserting the lens L upon an eye E (FIG. 4), as will be described more fully hereinafter. The locating means 15 is a relatively shallow, outwardly opening concave surface having an axis or radius of generation which is generally designated by the reference numeral 16. The radius 16 is approximately 0.395 inch and sets off or includes with the central axis 14 an angle a1 of generally 45 degrees.

The terminal end portion 13 is of a generally frusto-conical configuration terminating at its narrow end (unnumbered) in second means 25 for locating a contact lens L1 (FIG. 5) thereupon and adhering the same thereto incident to removing the lens L1 from an eye E1 (FIG. 5). The second means 25 is a static suction cup 26 having an extremely thin and pliable lip 27 and an outwardly opening concave surface 28 defined by a radius or axis of generation 30 which is approximately 0.195 inch, thus resulting in a curvature of the concave surface 28 which is relatively deeper than that of the concave surface 15. The axis of generation 30 defines with the central axis 14 an included angle a2 of generally 45 degrees, as is best illustrated in FIG. 2. Though the angle a1, a2 are equal, it should be particularly noted that the offset relationship of the locating means 15, 25 associated therewith is diametrically opposite, namely, the concave surfaces 15, 28 open in diametrically opposite directions. Furthermore, the axes of generation 16, 30 are parallel to each other and normal to a plane common thereto which is a vertical plane in FIG. 2. These relationships together with the included angles of 45 degrees (a1 and a2), are particularly important in that they provide an unobstructed view into an associated mirror M (FIG. 1), when the lens L or L1 is inserted upon or removed from an associated eye E or E1, respectively (FIGS. 4 and 5, respectively).

INSERTION

The body 11 of the device 10 is gripped in the manner shown in FIG. 1 with, of course, the contact lens L being adhered thereto by the capillary action between the wetting solution between the lens L and the surface 15, as is well known. With the lens L thus properly positioned upon the surface 15 and held thereto by the capillary action, the device 10 is then moved toward the eye while the user gazes in the mirror M to assist in the orientation and the insertion of the lens upon the eye E. Due to the offset created by the angle a1, the mirror M is totally visible, as is graphically illustrated in FIG. 1, and there is no possibility of inaccurately aligning the lens L relative to the eye E or causing damage to the latter. Thus, this complete visibility allows the user to accurately and gently apply the lens L to the eye E at which point the capillary action between the cornea or eye E and the lens L exceeds that between the lens L and the surface 15 causing the lens L to adhere to the eye E. The device 10 can now be readily removed from the eye area, and the lens L will simply be retained and remain upon the eye E.

REMOVAL

Removal of the contact lens L1 (FIG. 5) is effected much in the same manner as that just described, also in association with the mirror M of FIG. 1, but in this case the suction cup 26 is aligned with the eye E1 during which time the body 11 is held adjacent the terminal end portion 12. In this case, the offset angle a2 again permits total visibility of the eye E1 within the mirror M, and the suction cup 26 can be aligned with and then applied to the lens L1 by appropriate movement, as indicated by the unnumbered solid arrow in FIG. 5. The slight deflection of the periphery 27 and the attraction of the suction cup 26 is sufficient to attract the lens L1 against the suction surface 28 after which the device 10 can be moved away from the eye E1 in the direction of the unnumbered phantom arrow in FIG. 5 whereupon total removal (FIG. 6) again occurs with complete mirror M visibility and in the absence of accidental eye damage.

It is to be particularly noted that both during the insertion (FIG. 4) and removal (FIG. 5) of the lens L and L1, respectively, relative to an eye E and E1, respectively, the respective offset relationship of the means 15, 25 created by the respective angles a1, a2 preclude any type of obstruction of the image formed in the mirror M. This is particularly important in the case of users who suffer from very poor vision and must use a magnification miror of short focal length. One such popular mirror has a focal length of approximately 1½ inches which confines the space between the eye and the mirror and virtually precludes an unobstructed view of the ocular area during insertion or removal of contact lenses using conventional insertion/removal devices. However, due to the oppositely directed concave surfaces 15, 25, and the offset provided by the angles a1, a2, visibility during both insertion (FIG. 4) and removal (FIG. 5) is assured with the attendant assurance of accuracy which automatically precludes misalignment and/or eye damage.

Although only a preferred embodiment of the invention has been specifically illustrated and described herein, it is to be understood that minor variations may be made in the apparatus without departing from the spirit and scope of the invention, as defined in the appended claims.

I claim:

1. A device for inserting and removing hard contact lenses comprising an elongated body of resilient material having opposite terminal end portions, said elongated body including a central axis, static suction cup means at one of said terminal end portions for locating a hard contact lens at a predetermined angle to said central axis incident to placing the lens upon an eye, said static suction cup means being defined by a first static concave surface, soft resilient suction cup means at another of said terminal end portions for locating a hard contact lens at a predetermined angle to said central axis incident to removing the lens from an eye, said soft resilient suction cup means being defined by a body portion defined in part by a resilient peripheral lip and a second concave surface, said body portion and second concave surface being angularly offset relative to said central axis and defining therewith an acute angle, and said second concave surface being defined by a radius of generation which is disposed at an angle of generally 45 degrees to said central axis.

2. The device as defined in claim 1 wherein said first static concave surface is defined by a radius of generation which is disposed at an angle of generally 45 degrees to said central axis.

3. The device as defined in claim 1 wherein said elongated body includes a frusto-conical body portion narrowing in a direction toward said soft resilient suction cup means.

4. The device as defined in claim 1 wherein said first static concave surface is defined by a radius of generation which is disposed at an angle of generally 45 degrees to said central axis, and said radii of generation are generally parallel to each other.

5. The device as defined in claim 4 wherein said elongated body includes a frusto-conical body portion narrowing in a direction toward said soft resilient suction cup means.

* * * * *